(12) United States Patent  
Baldwin

(10) Patent No.: US 9,173,553 B2  
(45) Date of Patent: Nov. 3, 2015

(54) CONTROLLED PRESSURE ENDOSCOPIC AND PERCUTANEOUS SURGERY

(71) Applicant: FACULTY PHYSICIANS AND SURGEONS OF LOMA LINDA UNIVERSITY SCHOOL OF MEDICINE, Loma Linda, CA (US)

(72) Inventor: Dalton Duane Baldwin, Loma Linda, CA (US)

(73) Assignee: FACULTY PHYSICIANS AND SURGEONS OF LOMA LINDA UNIVERSITY SCHOOL OF MEDICINE, Loma Linda, CA (US)

( * ) Notice: Subject to any disclaimer, the term of this patent is extended or adjusted under 35 U.S.C. 154(b) by 0 days.

(21) Appl. No.: 14/528,054

(22) Filed: Oct. 30, 2014

(65) Prior Publication Data

US 2015/0119645 A1  Apr. 30, 2015

Related U.S. Application Data

(60) Provisional application No. 61/897,483, filed on Oct. 30, 2013.

(51) Int. Cl.
*A61B 1/04* (2006.01)
*A61B 1/00* (2006.01)
*A61B 1/015* (2006.01)

(52) U.S. Cl.
CPC ............. *A61B 1/015* (2013.01); *A61B 1/00135* (2013.01)

(58) Field of Classification Search
CPC ........................................................ A61B 1/125

USPC ................ 600/114, 202, 104, 118, 121, 136; 348/45, 65

See application file for complete search history.

(56) References Cited

U.S. PATENT DOCUMENTS

| 3,850,162 | A | * | 11/1974 | Iglesias ......................... 600/105 |
| 4,423,727 | A | * | 1/1984 | Widran et al. .................. 606/46 |
| 4,971,034 | A | * | 11/1990 | Doi et al. ....................... 600/104 |
| 5,125,058 | A | | 6/1992 | Tenerz et al. |
| 5,269,289 | A | * | 12/1993 | Takehana et al. ............. 600/109 |
| 5,807,240 | A | * | 9/1998 | Muller et al. .................. 600/135 |
| 5,810,776 | A | * | 9/1998 | Bacich et al. ................. 604/131 |
| 5,855,549 | A | * | 1/1999 | Newman ....................... 600/135 |

(Continued)

OTHER PUBLICATIONS

International Search Report and Written Opinion, re PCT App. No. PCT/US2014/063102, mailed Feb. 26, 2015.

*Primary Examiner* — Anhtuan T Nguyen
*Assistant Examiner* — Timothy J Neal
(74) *Attorney, Agent, or Firm* — Knobbe Martens Olson & Bear LLP

(57) ABSTRACT

The present disclosure relates to systems and methods for controlling pressure during percutaneous and endoscopic surgeries, including percutaneous renal procedures, endoscopic uterine procedures, transurethral endoscopic procedures for the bladder or prostate, or any percutaneous or endoscopic procedure. The system can include a sheath and/or endoscope each having an inflow port providing access to an inflow channel extending from the inflow port to a distal portion of the sheath, and an outflow port providing access to an outflow channel extending from the outflow port to the distal portion of the sheath. The sheath can also include a pressure sensor configured to generate a pressure measurement, and an electronic processor configured to control fluid through at least one of the inflow port and the outflow port based on the pressure measurement.

15 Claims, 11 Drawing Sheets

(56) References Cited

U.S. PATENT DOCUMENTS

| | | | |
|---|---|---|---|
| 6,086,542 A * | 7/2000 | Glowa et al. | 600/561 |
| 7,150,713 B2 * | 12/2006 | Shener et al. | 600/156 |
| 7,500,947 B2 * | 3/2009 | Kucklick et al. | 600/114 |
| 7,942,810 B2 * | 5/2011 | Uchimura et al. | 600/117 |
| 8,531,670 B2 * | 9/2013 | Schenkl et al. | 356/436 |
| 2005/0085695 A1 | 4/2005 | Shener et al. | |
| 2007/0213666 A1 * | 9/2007 | Barzell et al. | 604/131 |
| 2007/0270788 A1 * | 11/2007 | Nahen et al. | 606/15 |
| 2008/0091074 A1 * | 4/2008 | Kumar et al. | 600/156 |
| 2009/0062611 A1 * | 3/2009 | Toyama | 600/118 |
| 2009/0182201 A1 | 7/2009 | Kucklick et al. | |
| 2009/0326468 A1 | 12/2009 | Blier | |
| 2013/0310647 A1 * | 11/2013 | Milton et al. | 600/155 |

* cited by examiner

CONTROLLED PRESSURE ENDOSCOPIC AND PERCUTANEOUS SURGERY

PRIORITY APPLICATIONS

This application claims priority benefit under 35 U.S.C. §119(e) to U.S. Provisional Application No. 61/897,483, titled "CONTROLLED PRESSURE ENDOSCOPIC AND PERCUTANEOUS SURGERY," filed Oct. 30, 2013, which is hereby incorporated by reference in its entirety.

Any and all applications for which a foreign or domestic priority claim is identified in the Application Data Sheet as filed with the present application are hereby incorporated by reference under 37 CFR 1.57.

BACKGROUND

1. Field

The present disclosure relates to methods and devices for a closed percutaneous surgery.

2. Description of the Related Art

During percutaneous kidney stone surgery, a small puncture is made in the back or side of a patient to allow access into the kidney for removal of kidney stones, removal of tumors, or treatment of anatomic defects or strictures. In conventional (open system) percutaneous endoscopic procedures, a 30 F inner diameter sheath is placed into the kidney and used to facilitate introduction of either a rigid or flexible endoscope into the kidney. The endoscope is used to break up the stones or treat the tumor or anatomic abnormality. The rigid percutaneous endoscopes come in different sizes but are often 24 or 26 F in size, while the smaller flexible endoscopes are often 16 or 18 F in size.

SUMMARY

Certain aspects of the disclosure are directed toward a system for controlling pressure during endoscopic and percutaneous surgeries. The system can include an endoscope having a proximal portion and a distal portion. The endoscope can include an inflow port providing access to an inflow channel extending from the inflow port to the distal portion of the endoscope and/or an outflow port providing access to an outflow channel extending from the outflow port to the distal portion of the endoscope. The endoscope can also include a pressure sensor (e.g., at or near a distal portion of the endoscope). The pressure sensor can generate a pressure measurement. Further, the endoscope can include an electronic processor configured to control fluid through at least one of the inflow port and the outflow port based on the pressure measurement.

In the above-mentioned aspect, the endoscope can include an input control configured to receive a desired pressure value. In certain aspects, the processor can be configured to increase flow of an irrigant through the inflow port when the pressure measurement is less than the desired pressure value. In certain aspects, the processor can be configured to increase flow of a fluid out of the outflow port when the pressure measurement is greater than the desired pressure value.

Certain aspects of the disclosure are directed toward a system for controlling pressure during endoscopic and percutaneous surgeries. The system can include a sheath having a proximal portion and a distal portion. The sheath can include an inflow port providing access to an inflow channel extending from the inflow port to the distal portion of the sheath and/or an outflow port providing access to an outflow channel extending from the outflow port to the distal portion of the sheath. The sheath can also include a pressure sensor (e.g., at or near a distal portion of the sheath). The pressure sensor can generate a pressure measurement. Further, the sheath can include an electronic processor configured to control fluid through at least one of the inflow port and the outflow port based on the pressure measurement.

In the above-mentioned aspect, the sheath can include an input control configured to receive a desired pressure value. In certain aspects, the processor can be configured to increase flow of an irrigant through the inflow port when the pressure measurement is less than the desired pressure value. In certain aspects, the processor can be configured to increase flow of a fluid out of the outflow port when the pressure measurement is greater than the desired pressure value.

In the above-mentioned sheath aspects, the system can include a cap configured to close a proximal end of the sheath. In certain aspects, the cap can be configured to receive an endoscope.

Certain aspects of this disclosure are directed toward a system for controlling pressure during endoscopic and percutaneous surgeries. The system can include a sheath having a proximal portion and a distal portion. The sheath can include an inflow port providing access to an inflow channel extending from the inflow port to the distal portion of the sheath and/or an outflow port providing access to an outflow channel extending from the outflow port to the distal portion of the sheath. The sheath can also include a pressure sensor (e.g., at or near a distal portion of the sheath). The pressure sensor can generate a first pressure measurement. Further, the endoscope can include an electronic processor configured to control fluid through at least one of the inflow port and the outflow port based on the first pressure measurement. The system can also include an endoscope configured to be introduced through the sheath. The endoscope can include an inflow port providing access to an inflow channel extending from the inflow port to the distal portion of the endoscope and/or an outflow port providing access to an outflow channel extending from the outflow port to the distal portion of the endoscope. The endoscope can also include a pressure sensor (e.g., at or near a distal portion of the endoscope). The pressure sensor can generate a second pressure measurement. Further, the endoscope can include an electronic processor configured to control fluid through at least one of the inflow port and the outflow port based on the second pressure measurement.

In the above-mentioned system aspect, the system can further include a cap configured to close a proximal end of the sheath. The cap can be configured to receive the endoscope.

Certain aspects of this disclosure are directed toward a method of controlling pressure in a renal collecting system. The method can include positioning a distal end of an endoscope in the collecting system; measuring the pressure in the collecting system; and controlling fluid flow through the endoscope based on the pressure measurement. The endoscope can include an inflow port providing access to an inflow channel extending from the inflow port to a distal portion of the endoscope and/or an outflow port providing access to an outflow channel extending from the outflow port to the distal portion of the endoscope. The endoscope can also include a pressure sensor. The pressure sensor can be configured to generate a pressure measurement. The endoscope can also include an electronic processor configured to control fluid through at least one of the inflow port and the outflow port based on the pressure measurement.

The above-mentioned method can also include inputting a desired pressure value into an input control of the endoscope. In certain aspects, the processor can be configured to increase flow of an irrigant through the inflow port when the pressure measurement is less than the desired pressure value. In certain aspects, the processor can be configured to increase flow of a fluid out of the outflow port when the pressure measurement is greater than the desired pressure value.

Certain aspects of this disclosure are directed toward a method of controlling pressure in a renal collecting system. The method can include positioning a distal end of a sheath in the collecting system; measuring the pressure in the collecting system; and controlling fluid flow through the sheath based on the pressure measurement. The sheath can include an inflow port providing access to an inflow channel extending from the inflow port to a distal portion of the sheath and/or an outflow port providing access to an outflow port extending from the outflow port to the distal portion of the sheath. The sheath can also include a pressure sensor. The pressure sensor can be configured to generate a pressure measurement. The sheath can also include an electronic processor configured to control fluid through at least one of the inflow port and the outflow port based on the pressure measurement.

The above-mentioned method can also include inputting a desired pressure value into an input control of the sheath. In certain aspects, the processor can be configured to increase flow of an irrigant through the inflow port when the pressure measurement is less than the desired pressure value. In certain aspects, the processor can be configured to increase flow of a fluid out of the outflow port when the pressure measurement is greater than the desired pressure value.

In certain aspects, the efflux can be monitored by a sensor on the efflux monitor. In routine percutaneous nephrostolithotomy, as the surgeon is working, the influx drains from large two to four liter bottles of saline. This saline flows into the kidney at a rapid rate and the saline then flows out of the kidney at a rapid rate between the space between the nephroscope and the inner diameter of the sheath. The open system facilitates the rapid flow of irrigation. A rapid flow of irrigation may be beneficial when there is a lot of bleeding or if the stone pieces are fragmenting rapidly might obscure the surgeons view. However, in some circumstances, there is minimal bleeding and the hard stone is fragmenting slowly such that high flow rates are not required. With this system for closed percutaneous surgery, the system could be operated in a fluid conservation mode. In this mode, a sensor in the efflux channel or at the tip of the scope can measure light transmission across the efflux in such a manner that if the light transmission has been degraded by blood or particulates the sheath could increase the inflow and outflow automatically maintaining pressure and optimizing visualization. If the efflux had no particulates and no blood, the transmission of light is not impeded and the device could slow down the flow of the irrigation fluid to conserve the fluid efflux.

During the treatment of a large staghorn calculus, it is not unusual to consume more than 400 liters of saline and during large cases the waste disposal of empty bottles, hanging of fluids, procuring new fluid bottles and emptying old fluid bottles can consume the time of one staff member. Furthermore, if this staff member does not notice when the irrigation is getting low the procedure may be temporarily suspended due to lack of irrigation until new bottles are obtained. In rare circumstances, the hospital may even run out of irrigation resulting in premature termination of the procedure. Hence the ability to operate on conserve mode when the irrigation is clear and doesn't need high flow rates could save money due to use of less irrigation bottles, require less staff in the operating room, require less effort to clean up the floor and significantly decrease the waste disposal and make the operating room more green.

In another embodiment the nephroscope itself could have a sensor that would measure the blood and particulates and give feedback to the device which would automatically increase or decrease the flow rate.

In conventional percutaneous nephrostolithotomy the saline that goes in to the patient subsequent is mixed with the patient's blood inside the renal pelvis and then subsequently drains outside the sheath and onto the flank of the patient. There are drapes that are designed to maintain a seal with the patient, but invariably, fluid escapes underneath the drape and dribbles down the side of the patient and subsequently ends up on the floor where it may short out the electrical switches that the surgeon is using to operate the foot pedals designed to operate equipment. This bloody saline effluent may contain hepatitis, AIDS, or other infectious diseases and subsequently the surgeon is exposed to these infectious organisms due to their feet and legs being constantly wet. The ability to turn open into closed percutaneous surgery may significantly reduce the infectious risk for the surgeon as the fluid flow would be maintained in a closed system and leakage would be much less. In addition, the floor would not be wet and require separate suction devices or blankets placed by the nurse to keep the staff from sustaining an injury due to slipping on the floor.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

Figure 1:
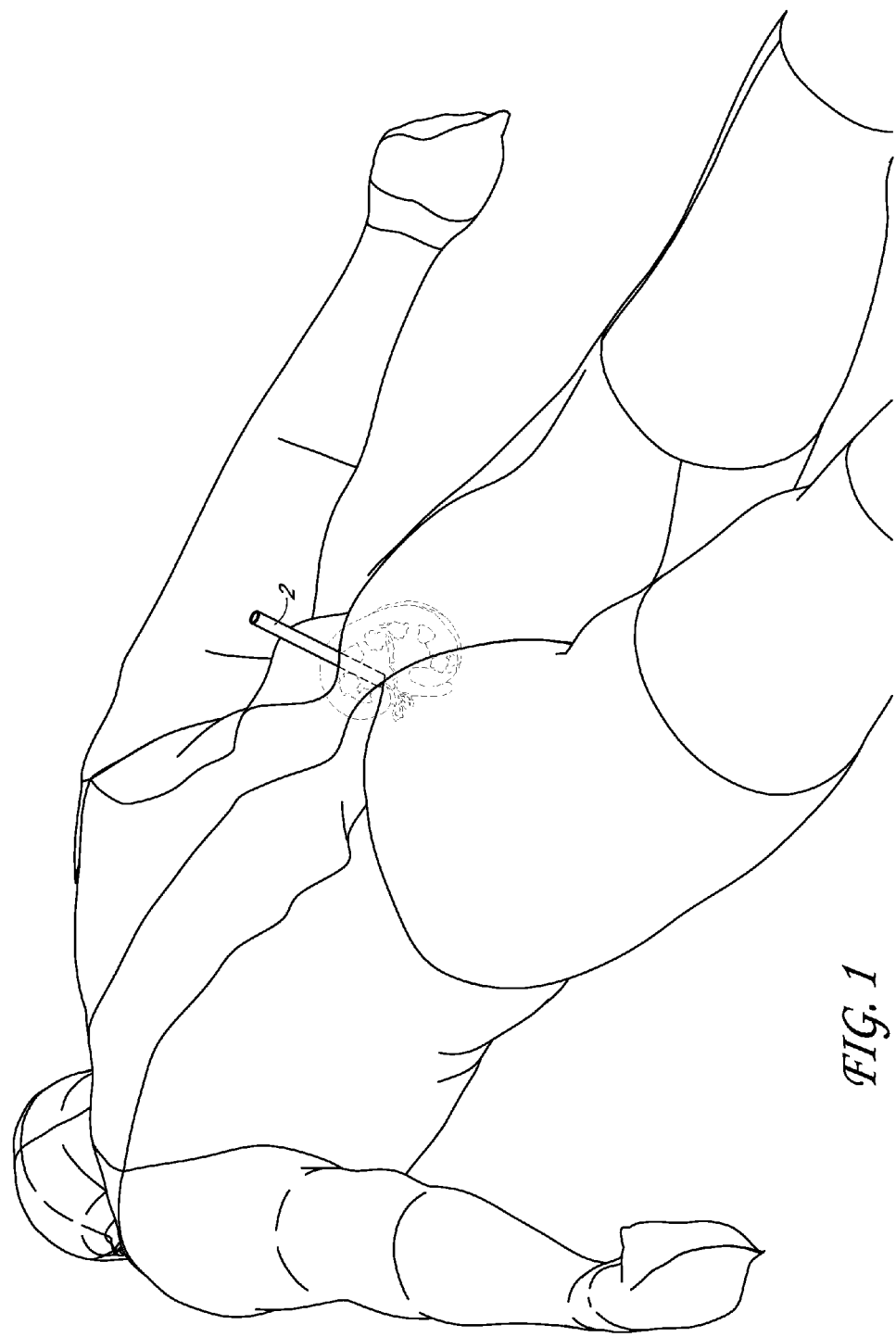
FIG. 1 illustrates a percutaneous access sheath inserted into a patient.

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

Open surgery can be problematic because there is no pressure to limit bleeding vessels and the system is open to bacterial infection, drying, and other physiologic changes. Similarly, endoscopic surgery, in particular percutaneous intrarenal surgery, today is performed in an open fashion where the pressure is not controlled and alterations in the intrarenal pressure may have serious consequences. Pressures that are too low may result in excessive venous bleeding, impaired visibility, and collapse of the renal collecting system. Pressures that are too high may rupture the renal collecting system and increase opportunities for bacteria and fluids to move into the intravascular space or perinephric space, potentially resulting in fluid shifts and even urosepsis.

There can be tremendous variation in intrarenal pressures during percutaneous renal surgery depending on the type of endoscope, number of tracts, and position of the tracts. A smaller, flexible endoscope allows a surgeon to navigate the anatomy to access portions of the kidney that are not ordinarily accessible with a straight, rigid endoscope, thereby decreasing the number of access sites. However, the irrigant flow through the smaller, flexible endoscope is less than the irrigant flow through the larger, rigid endoscope. Further, the amount of space between the flexible endoscope and the sheath is significantly greater than the amount of space between the rigid endoscope and the sheath. If a 26 F rigid endoscope is introduced through a 30 F inner diameter sheath, there remains only a small amount of space for irrigation outflow. By comparison, if a 16 F flexible endoscope is introduced through a 30 F sheath, there remains a very large amount of space for outflow. In addition, when switching from a rigid endoscope to a flexible endoscope, the irrigant draining from the tract becomes bloodier, in many instances making it difficult to visualize the anatomy when using the flexible endoscope.

The pressure in the renal collecting system is significantly decreased when irrigating with the smaller, flexible endoscope compared to the larger, rigid endoscope. A lower pressure inside the renal collecting system decreases the ability to visualize the anatomic structures inside the renal collecting system. This decreased visualization stems from two negative effects. First, increased blood content in the renal collecting system causes dense pigments like hemoglobin to be in the saline irrigation. The pigments absorb the light energy and decrease visualization. Second, with a lower pressure, the renal collecting system usually appears collapsed, making it difficult to visualize the internal anatomy of the kidney and to identify specific calices and stones in those calices. The collapsed folds of the renal collecting system also make it difficult to maintain the orientation of the endoscope while inside the kidney and may make it difficult to identify the opening into a specific calix bearing pathology (stone or tumor).

An alternative strategy to using the flexible endoscope is to use multiple access tracts in an attempt to remove stones located at sites that cannot be reached using the rigid endoscope from the primary access site (see FIG. 1). FIG. 1 illustrates a patient with a standard sheath 2 inserted percutaneously. The use of a second access site can improve irrigation flow by reducing the resistance to the outflow of saline irrigation. However, despite the better irrigant flow rate, visualization can still be impaired, as the pressure in the collecting system has been shown to drop down to close to the baseline pressure when a second access sheath is in place. In addition, patients receiving two nephrostomy tracts experience a larger amount of bleeding and have a significantly greater risk of requiring a blood transfusion. When using two tracts, the pressure can still be too low to provide tamponade of venous bleeding and to maintain expansion of the collecting system making it more difficult to see the collecting system and harder to locate the pathology.

Percutaneous tracts placed vertically can increase the pressure in the renal collecting system. The vertical tract can create a column of fluid that fills the nephrostomy tube and places additional pressure on the collecting system. Any pressure in the collecting system that is below the pressures in the renal capillaries, veins, or veinules can increase venous bleeding from the kidney, which can increase the patient's blood loss. In contrast, pressures inside the renal collecting system that are higher than the pressures in the renal capillaries, veins or veinules will decrease the amount of bleeding that the patient experiences. The increased blood loss increases the likelihood of needing a transfusion and increases surgical risks associated with increased fluid shifts. In addition, if the pressure is too high, the collecting system may rupture. Further, there is an increased risk of pyelovenous backflow and pyelolymphatic backflow, which can introduce bacteria into the bloodstream and increase the risk of sepsis. In the face of collecting system injury, if pressures are too high, there can also be an increase in absorption of fluids with the subsequent risk of fluid overload in patients.

Additional factors including, but not limited to, the height of the fluid irrigation source, the fluid level inside the irrigation containers, the angle of the nephrostomy tube, and the depth of skin, fat, and subcutaneous tissues, can all affect the pressure inside the renal collecting system.

Given the drawbacks listed above, there is a need to control fluid inflow and outflow during percutaneous procedures. The advantages would be decreased blood loss, better exposure to the intrarenal anatomy, shorter operative time and improved surgical outcomes.

Cap System

As described above, the use of a second access site can improve irrigation flow by reducing the resistance to the outflow of saline irrigation. However, patients receiving two nephrostomy tracts experience a larger amount of bleeding and have a significantly greater risk of requiring a blood transfusion. In these scenarios, it can be desirable to control irrigant flow and pressure by closing off one of a multiple number of percutaneous access sheaths. The cap 4 can limit outflow of irrigation until a prescribed pressure is reached (see FIG. 2).

A common instance in which the cap 4 would be utilized is during a percutaneous nephrostolithotomy with a single tract in place. In this instance, the surgeon will be working at a mean renal pelvic pressure of 20-35 mm Hg using the high flow rigid nephroscope. The system will be expanded and the different calices would be easy to identify. Once the surgeon has removed all of the stone that can be reached using the straight rigid nephroscope, the surgeon would next need to move to a 16 French flexible nephroscope. In open percutaneous surgery, the pressure inside the renal pelvis immediately drops from 20-35 down to 5-10 mm of Hg. The renal pelvis collapses and the surgeon has a hard time identifying the takeoffs to calices and is more likely to cause injury to the urothelium while employing holmium laser lithotripsy. Using the cap 4, the outflow can be reduced when the surgeon is operating with a smaller scope and the pressure can be maintained at 20-30 mm Hg. The surgeon will still able to visualize the takeoffs to the calices, and because the system remains distended, there is less blood loss and less of a chance for injury to the urothelium.

Another instance in which the occlusion cap 4 might be utilized is if the surgeon has obtained access in one portion of the kidney and has completed the removal of the stone in that portion of the kidney and now needs to move to another portion of the kidney to treat stone. In the new location, the surgeon could apply a new second access sheath in another area and begin working in this second area with the rigid nephroscope. However, since the new access site communicates with the original access site the fluid would flow in through the rigid nephroscope in the new access site, but would flow out of both the first and second access sites. Since the outflow is so high, the fluid pressure in the collecting system would be very low, the surgeon would have increased bleeding, and decreased turgidity of the collecting system of the kidney meaning it would be more difficult to work without grinding on the transitional lining.

The cap 4 could be placed on the second tract to occlude flow so that the pressure can be maintained while working through the second tract. As another example, if there is so much bleeding that the surgeon cannot see even when using only one access sheath with a rigid scope, the surgeon can use the cap 4 to maintain a higher pressure when using the rigid scope with a conventional access sheath. This cap 4 could be used very simply with routine, currently available percutaneous access sheaths to maintain the pressure in the collecting system. This cap 4 could also be a component of the closed percutaneous surgery system where the pressure and flow were specifically controlled using the sheath model or the specially designed nephroscope described below. The inflow and outflow of conventional percutaneous nephroscopes could be used to maintain the pressure at the desired level with the cap 4 to turn the system from an open system to a closed system.

To reduce the amount of irrigation fluid used during the procedure, the entire system can be completely closed by filtering the irrigation fluid through a high level filter designed to filter out all bacteria, crystals, cells, and particulates and recirculating the filtered fluid back into the patient such that the irrigation bottle would never need to be changed during the entire case, freeing up the circulating nurse for other activities in the operating room.

Figure 2:
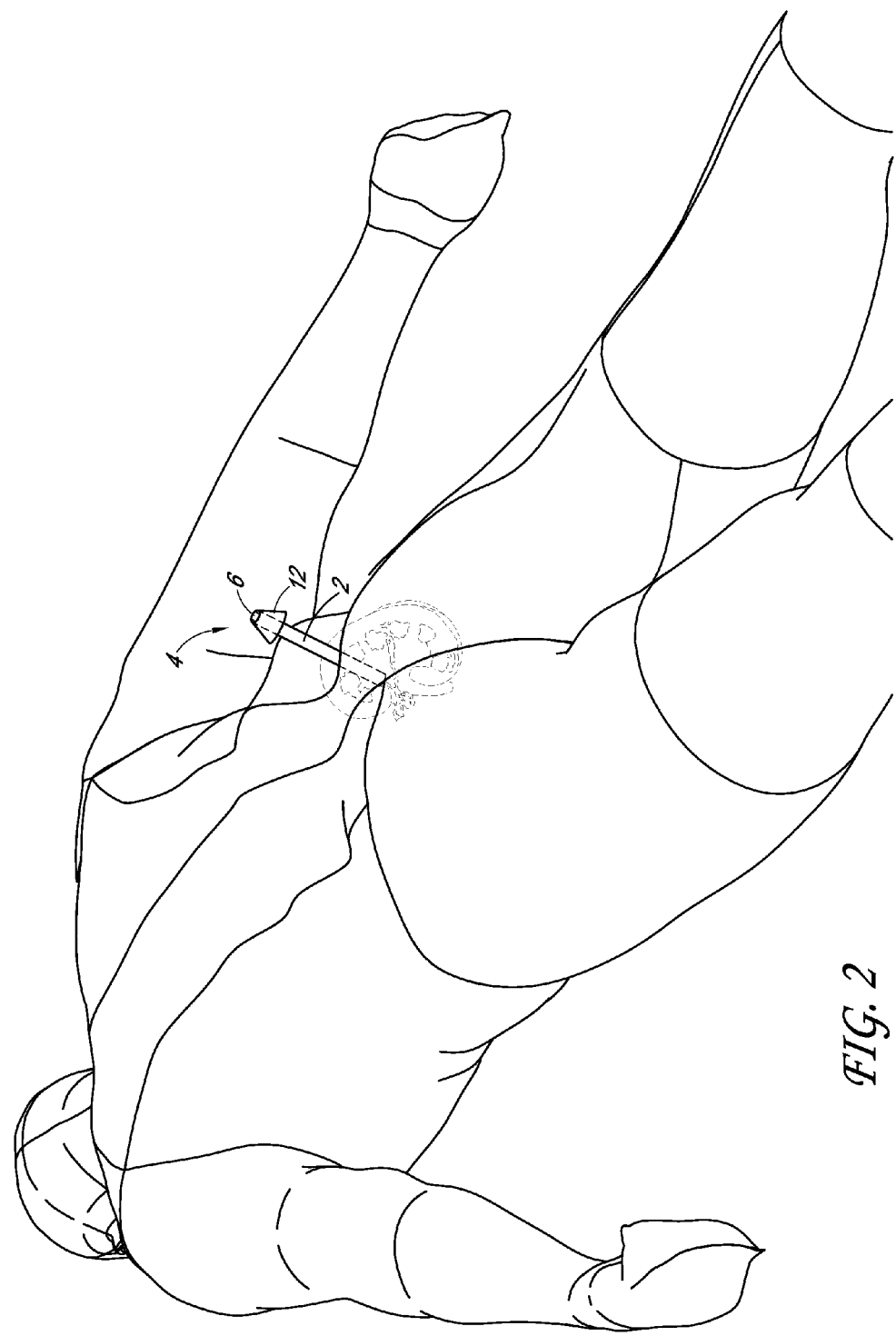
FIG. 2 illustrates a system with an embodiment of a cap secured to the percutaneous access sheath.

As shown in FIG. 2, a proximal end of at least one of the percutaneous access sheaths 2 can be closed off using the cap 4 having main body portion including a closed end 6 and a wall portion 12. The cap 4 can be sized such that an inner surface of the cap 4 surrounds an outer surface of the sheath 2. For example, if the sheath 2 has an outer diameter of at least 33-34 F with an inner diameter of 30 F, the cap 4 can be at least about 33-34 F, such as between about 30 F and about 35 F. The wall portion 12 can be between about 2 mm and about 20 mm long, for example, about 8 mm long or about 10 mm long. The cap 4 can be generally frustoconical, cylindrical, or any other shape suitable to surround the sheath 2.

The cap 4 can be secured to the sheath 2 using any connection mechanism, including, but not limited to, a screw fit, a snap fit, or a friction fit. Further, the cap 4 can be constructed from a variety of materials, including, but not limited to, rubber, plastic, silicone, polyurethane, or PTFE, so the cap 4 can be adaptable to different sized sheaths and/or form a friction fit with the sheath 2.

Figure 3:
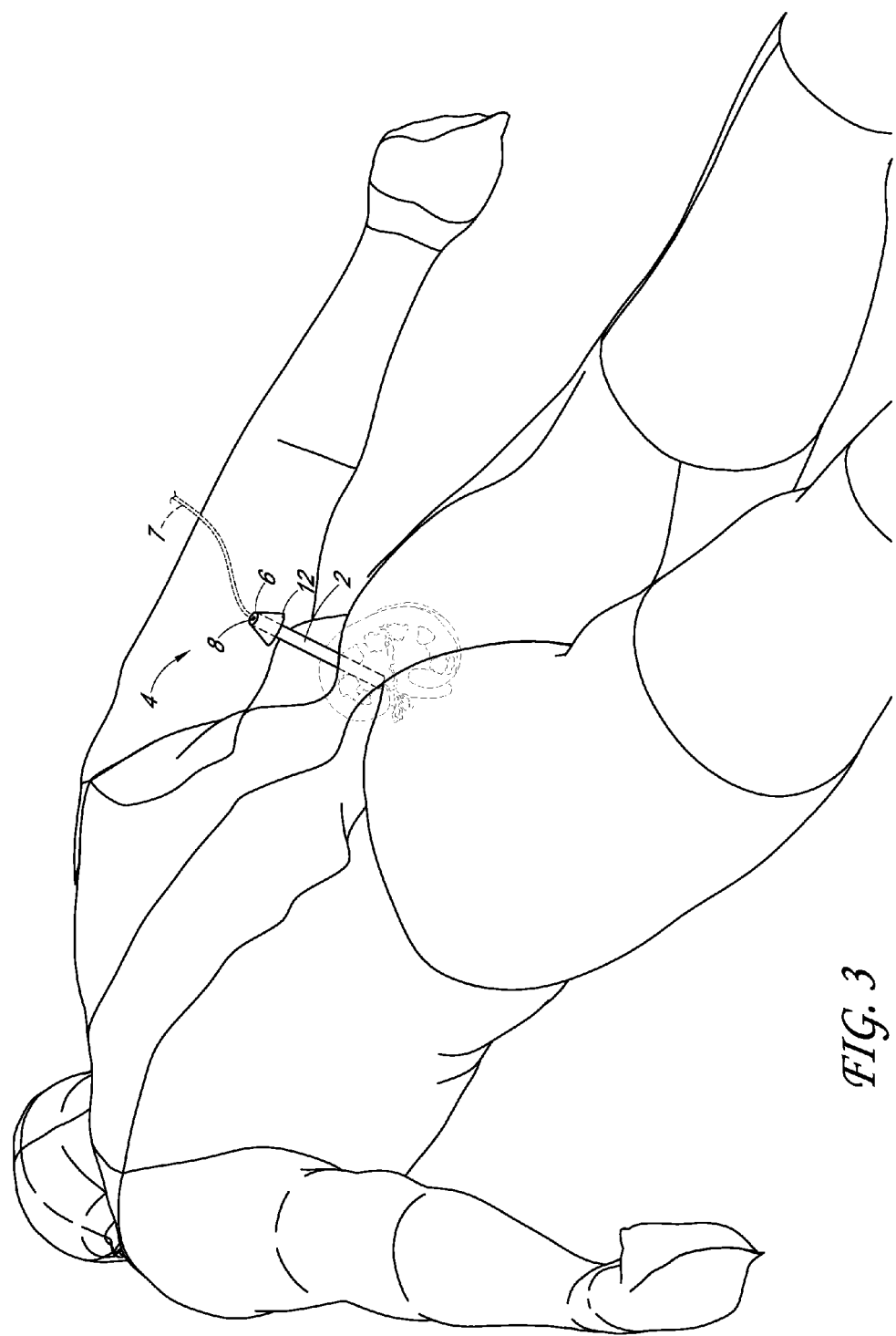
FIG. 3 illustrates a system with an endoscope extending through another embodiment of a cap secured to the percutaneous access sheath.

As shown in FIG. 3, the closed end 6 of the cap 4 can include an opening 8 sized to permit insertion of an endoscope 7. The opening 8 can be sized to accommodate different sized endoscopes or different caps 4 can be used for different sized endoscopes. The opening 8 can be between at least about 1 F and/or less than or equal to about 28 F depending on the size of the endoscope. If the opening 8 is sized to receive a large, rigid endoscope, the opening 8 can include a diameter that is at least about 20 F, for example, between about 20 F and about 24 F or between about 24 F and about 28 F. If the opening 8 is sized to permit insertion of a smaller, flexible endoscope, such as an ureteroscope, a diameter of the opening 8 can be between about 4 F and about 12 F, such as about 4 F, about 6 F, about 8 F, about 10 F, or about 12 F. For a cytoscope, the diameter of the opening 8 can be between about 8 F and about 20 F. It may be desirable for the opening 8 to be larger than the endoscope to provide additional space for irrigant outflow and prevent excess friction between the endoscope and the sheath.

Figure 4:
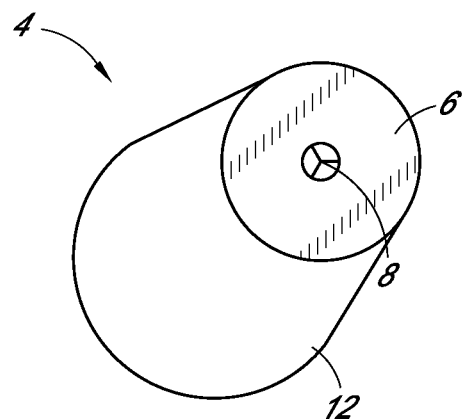
FIG. 4 illustrates a perspective view of the cap shown in FIG. 3.

As shown in FIG. 4, a sealing feature 10 can be positioned in the opening 8 to form a seal around the endoscope 7. The sealing feature 10 can be a self-sealing valve, such as a slit valve or a flap valve. For example, the sealing feature 10 can include a number of flaps adapted to form a seal around the endoscope and prevent the escape of fluids. The sealing feature 10 can be configured to release fluid above a set pressure. The set pressure can be between about 10 and 40 mm Hg, for example, between about 18 and 25 mm Hg, such as about 20 mm Hg.

Figure 5:
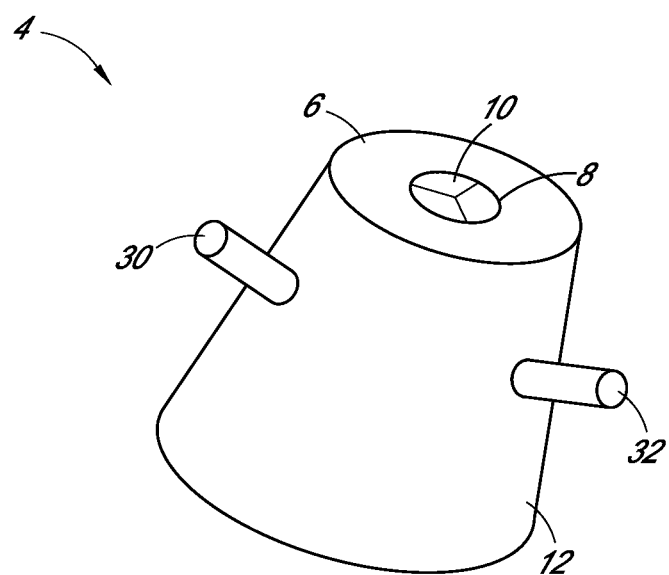
FIG. 5 illustrates a perspective view of yet another embodiment of the cap having inflow or outflow ports.

FIG. 5 illustrates another embodiment of the cap 4. The cap 4 can include any of the features described in connection with FIG. 4. Additionally, the cap 4 can include one or more ports 30, 32 positioned on main body portion of the cap 4.

Figure 6:
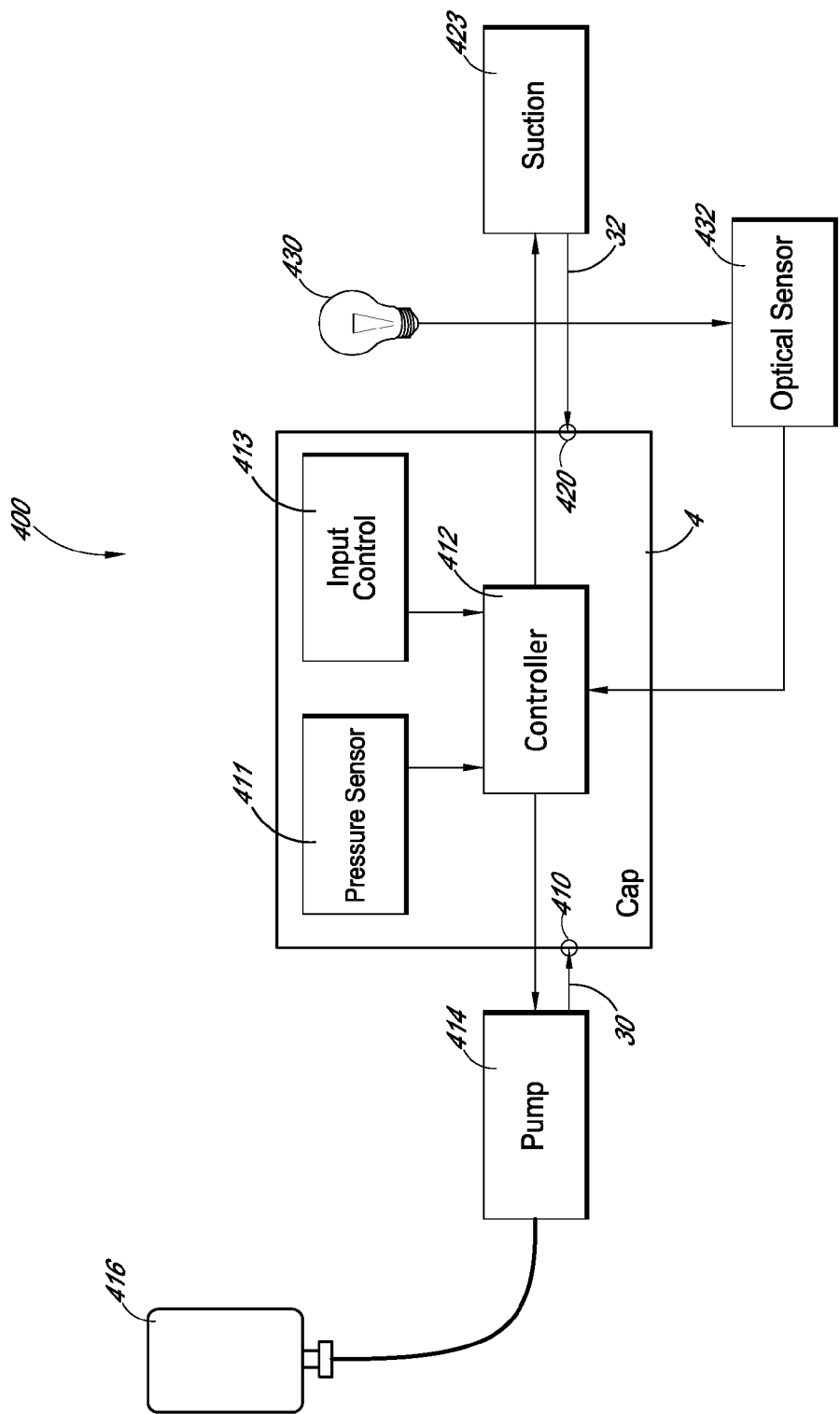
FIG. 6 is a schematic representation of a system including the cap shown in FIG. 5.

As shown in FIG. 6, in a cap system 400, the inflow port 30 can provide access from an irrigation source 416 to a main lumen of the sheath 2 via inflow tubing 418. The inflow port 30 can be sized to allow sufficient irrigation fluid to flow from the irrigation source 418 through the inflow port 30, for example with the aid of a pump 414. The cap 4 can include an outflow port 32 that provides an outlet for fluid flowing out of the sheath 2. The outflow port 32 can be sized to allow fluid to flow out of the port to maintain visualization within the collecting system in the body. Without a suction source, fluid can flow out of the outflow port 32 passively by gravity and pressure gradients. However, the outflow port 32 can be connected to a valve and/or suction source 423 via outflow tubing 422 to control outflow.

The cap 4 can include one or more pressure sensors 411 configured to detect the pressure within system. The pressure sensor 411 can be positioned anywhere on the cap 4 (e.g., in the outflow port), in the inflow tubing 418, the outflow tubing 422, or elsewhere in the system (e.g., sheath or endoscope). The pressure measurements can be transmitted to a controller 412 in the cap 4 or connected to the cap 4. The pressure sensor can be hardwired to transmit information to the controller 412 or to transmit the information wirelessly.

The controller 412 can include a processor configured to calculate the pressure within the collecting system in the body based on the pressure sensor measurement and subsequently automatically control fluid inflow and outflow based on the pressure measurement. This can be helpful where high flow is needed to clear bleeding, but pressure must still be maintained to have a tamponade effect upon venous bleeding. This could also be configured and operated in the fluid conservation mode if the fluid were not being recycled so that the pressure could be maintained with minimal flow of irrigation fluid.

The cap 4 can be connected to an input control 413, so the surgeon can enter a desired renal collecting system pressure into the input control. Based on the pressure sensor measurements, the controller 412 can control, by various algorithms, the inflow and outflow of fluid through the cap 4 and sheath 2, thereby controlling the pressure in the collecting system. If the collecting system pressure exceeds the desired pressure, fluid flow out of the outflow port 32 can be turned on or increased until the pressure decreases to the desired level. Once the desired pressure is achieved, the outflow of saline can be automatically decreased or stopped. If the pressure is too low, the pump 414 can begin pumping or increase pumping from a saline bottle via the inflow port 30 until the desired pressure is achieved. Once the desired pressure is achieved, the inflow of saline can be automatically decreased or stopped.

The controller 412 can also take into consideration the amount of visibility in the renal collecting system. For example, one or more optical sensors 432 on the cap 4 or connected to the cap 4 can sense when the visibility is not clear and automatically adjust the inflow and/or outflow to maintain a clear irrigation field and a set pre-established pressure. A light 430 can be shined across the outflow tubing 422, inflow tubing 418, and/or sheath 2 and registered by an optical sensor 432 positioned opposite the light emitter (see FIG. 6). Blood or debris that decreases the absorption of light by the sensor 432 could signal the controller to increase the rate of suction by the source of suction 423 and/or to increase the pump rate of the pump 414 to increase inflow, thereby maintaining the same pressure and improving visibility.

Figure 7:
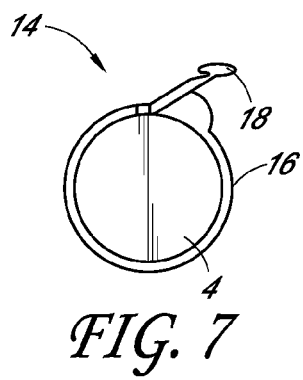
FIG. 7 illustrates a top view of yet another embodiment of a cap having a closure mechanism.
Figure 8:
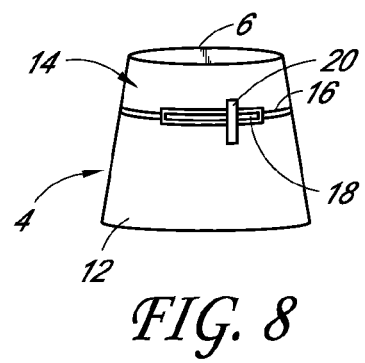
FIG. 8 illustrates a perspective view the cap shown in FIG. 7 with the closure mechanism in a closed configuration.
Figure 9:
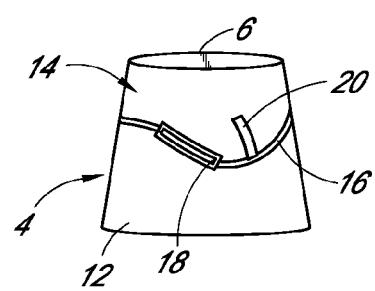
FIG. 9 illustrates a perspective view of the cap shown in FIG. 8 with the closure mechanism in an open configuration.

In some embodiments, the cap 4 can include a closure mechanism 14 to secure the cap 4 to the sheath 2 (see FIGS. 7-9). The closure mechanism 14 can be configured to move between an open position and a closed position in which the closure mechanism 14 applies pressure to the cap 4 to secure the cap 4 to the sheath 2. The closure mechanism 14 can be adjustable for securing the cap 4 to different sized sheaths or a single cap 4 can include different sized closure mechanisms for different scope sizes.

As shown in FIGS. 7-9, the closure mechanism 14 can include a cinching feature 16 circumferentially disposed around the wall portion 12 of the cap 4 and secured to the cap 4 at one or more positions around the cap 4. The cinching feature 16 can include one or more wires or bands constructed from a polymer or metal (e.g., stainless steel, nitinol, rubber, or plastic). Each wire or band can include a single filament or include a multiple number of filaments braided together for added strength. Each wire or band can include a width between about 0.1 mm and about 10 mm, such as between about 0.5 and about 4 mm.

The cinching feature 16 can include a tab 18 configured to move between an open position and a closed position. When the tab 18 is in the open position, the cinching feature 16 has a perimeter that is larger than a circumference of the cap 4 (see FIGS. 7 and 9). When the tab 18 is in the closed position, the perimeter of the cinching feature closes around the cap 4 to hold the cap 4 in place (see FIG. 8). The closure mechanism 14 can include a latch 20 secured over the cinching feature 16 to hold the cinching feature 16 and/or tab 18 in a closed position.

Figure 10:
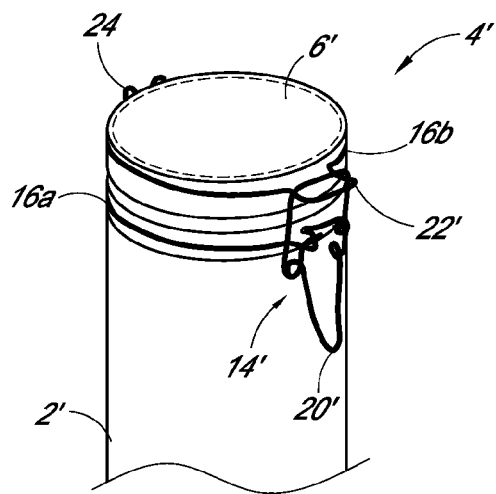
FIG. 10 illustrates a perspective view another embodiment of a cap secured to the percutaneous access sheath.
Figure 11:
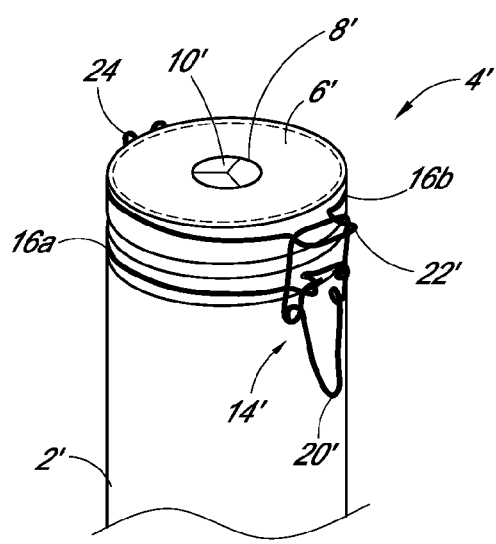
FIG. 11 illustrates a perspective view of yet another embodiment of the cap secured to the percutaneous access sheath.

FIG. 10 illustrates another exemplary embodiment of a cap 4' having a closure mechanism 14' that secures a movable closed end portion 6' to the cap 4'. The closure mechanism 14' can include a first band portion 16a and a second band portion 16b. When the cap 4' is secured to the sheath 2', the first band portion 16a can be circumferentially disposed around the sheath 2', while the second band portion 16b can be circumferentially disposed around the closed end portion 6'. In certain aspects, the sheath 2' can include a circumferential groove in which the first band portion 16a is disposed. As shown in FIG. 11, the cap 4' can include an opening 8' with a sealing structure 10' for receiving an endoscope.

The first and second band portions 16a, 16b can be constructed from a polymer or metal (e.g., stainless steel, nitinol, rubber, or plastic). Each band portion 16a, 16b can include a single filament or include a multiple number of filaments braided together for added strength.

The first and second band portions 16a, 16b can extends 360° around the sheath or closed end portion 6', or less than 360°, such as between about 270° and about 300°, between about 300° and about 300°, or between about 330° and about 360°.

A thickness of the second band portion 16b can be less than or equal to a thickness of the first band portion 16a.

A diameter of the second band portion 16b can be less than or equal to a diameter of the first band portion 16a. Each band portion 16a, 16b can include a width between about 0.1 mm and about 10 mm, such as between about 0.5 and about 4 mm.

The first band portion 16a can connect to the second band portion 16b such that the second band portion 16b can move relative to the first band portion 16a. The closure mechanism 14' can include connector 24', such as a hinge that permits the closed end portion 6' to move between an opened position and a closed position in which the closed end portion 6' covers, plugs, or otherwise closes the end of the sheath 2'.

The closure mechanism 14' can include a latch 20' for securing the first band 16a relative to the second band 16b. The latch 20' can be secured to the first band 16a and configured to engage a protruding feature 22' on the second band 16b.

Although not shown, the cap could alternatively be a plug shaped to fit within a lumen of the sheath. In certain aspects, the plug can be tapered to prevent the plug from slipping completely inside the sheath. In certain aspects, a diameter of an end portion of the plug can be greater than an internal diameter of the sheath to prevent the plug from slipping completely inside the sheath.

Figure 12:
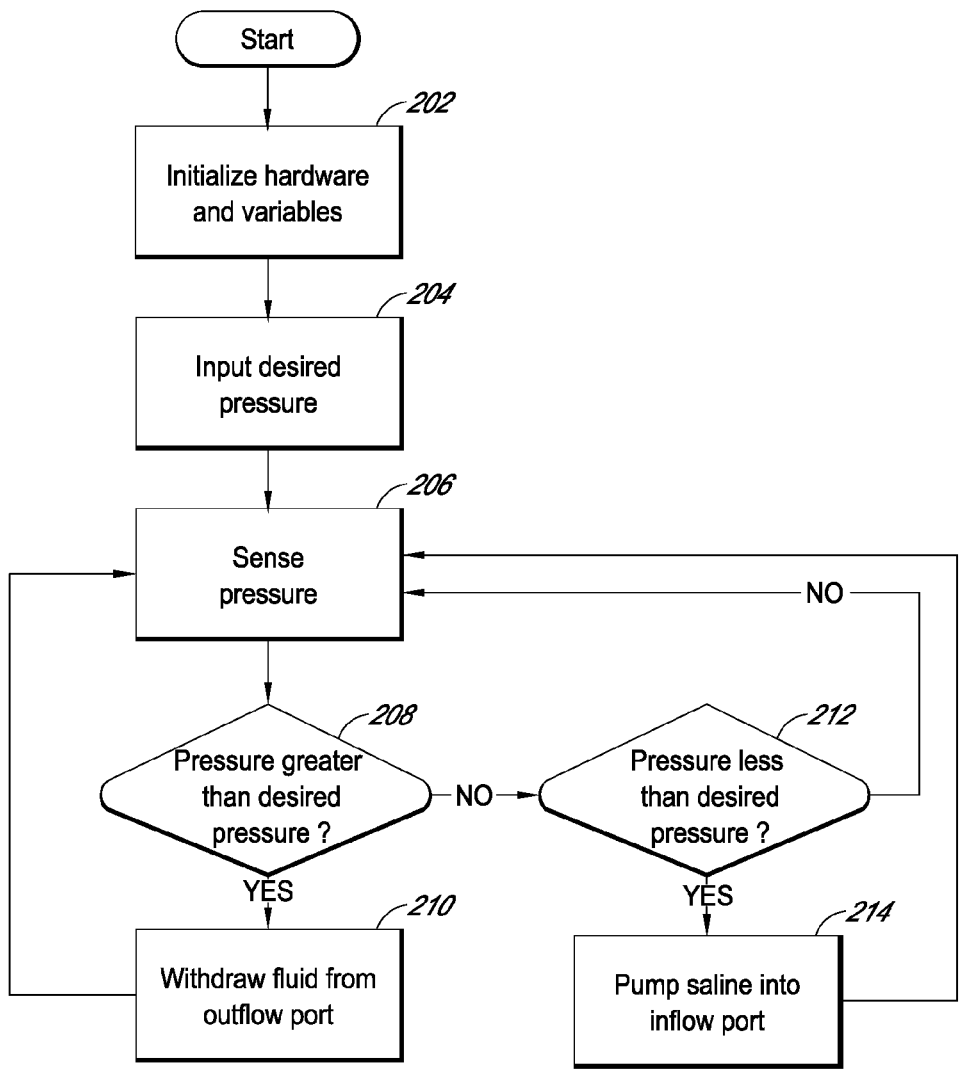
FIG. 12 illustrates a block diagram of an embodiment of a process that can be carried out by a system including the cap, the sheath, and/or the endoscope.

FIG. 12 is a flow chart illustrating a process for controlling fluid flow through the cap 4. After the hardware and variables are initialized (block 202), the user can set the desired pressure (block 204). Thereafter, the pressure sensor 411 begins to detect the pressure (block 206). These pressure readings can be taken constantly, periodically, or on command. The pressure readings could be taken many times a second and/or continuously adjusted so that the pressure variations were minimized. The pressure readings are transmitted to the controller 412. If the pressure sensor 411 is displaced from the collecting system in the body, the controller 412 can calculate the collecting system pressure based on the pressure measurement. If the collecting system pressure exceeds the desired pressure (block 208), then the controller 412 directs the source of suction 423 to increase fluid outflow (block 210). Fluid is withdrawn until the collecting system pressure reaches the desired pressure. If the collecting system pressure is too low (block 212), then the controller 412 directs the pump 414 to increase saline inflow through the sheath (block 214). Saline is continuously pumped into the sheath until the collecting system pressure reaches the desired pressure.

Figure 13:
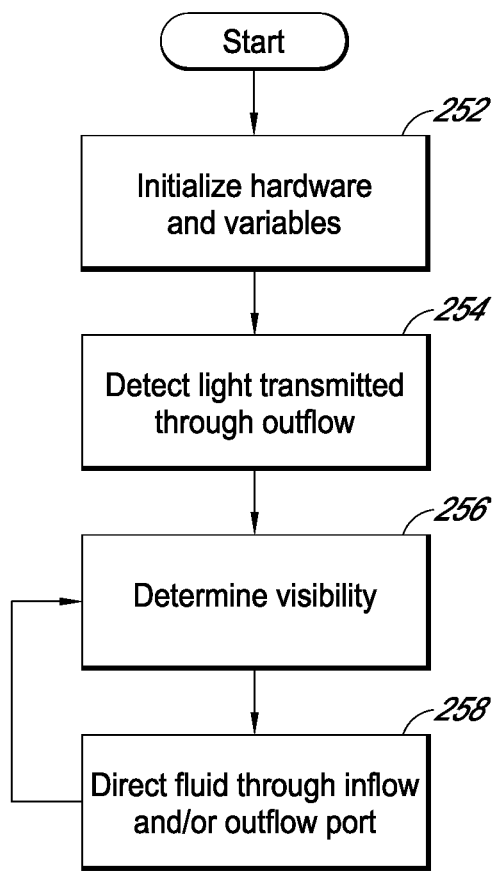
FIG. 13 illustrates a block diagram of another embodiment of a process that can be carried out by a system including the cap, the sheath, and/or the endoscope.

FIG. 13 illustrates another process for controlling fluid flow through the sheath 2. The hardware and variables are initialized (block 252), which can include emitting light across fluid outflow from the sheath, e.g., across outflow tubing 422 extending from the outflow port 32. An optical sensor 432 opposite the light transmitter 430 can detect the amount of light transmitted through the fluid outflow by detecting the amount of light not absorbed by the fluid outflow (block 254). The amount of detected light is indicative of the visibility in the surgical field. The readings can be taken constantly, periodically, or on command. The readings can be taken many times a second and/or continuously adjusted so the visibility in the surgical field is maintained. The levels of detected light are transmitted to the controller 412. If the amount of detected light is indicative of reduced visibility in the surgical field (block 256), the controller 412 can direct fluid flow through the inflow port and/or outflow port (block 258). For example, if less than 98% of the light emitted is detected by the optical sensor or less than about 95% of the light emitted is detected by the optical sensor, then the controller 412 can increase the rate of inflow or outflow to clear the field.

Although the flow charts in FIGS. 12 and 13 illustrate a feedback mechanism for controlling both inflow and outflow, in some instances, the cap 4 only includes an inflow port 30 or an outflow port 32. In some instances, even if the cap 4 includes both inflow and outflow ports 30. 32, the controller 412 only controls fluid through one port. For example, the controller 412 may control fluid inflow through the inflow port 410 based on the pressure readings, but fluid outflow through the outflow port may be continuous at all times, passively by gravity and pressure gradients. Alternatively, the outflow can be controlled by the operator (e.g., slow, medium or high flow), while the inflow can automatically adjust the inflow to a rate to maintain the pressure that was set, or vice versa. Outflow or inflow can be set to a scale such as 1-10, or a rate of flow such as 1 cc/sec/5 cc/sec/10 cc/sec, etc.

Pressure-Controlling Sheath

Figure 14:
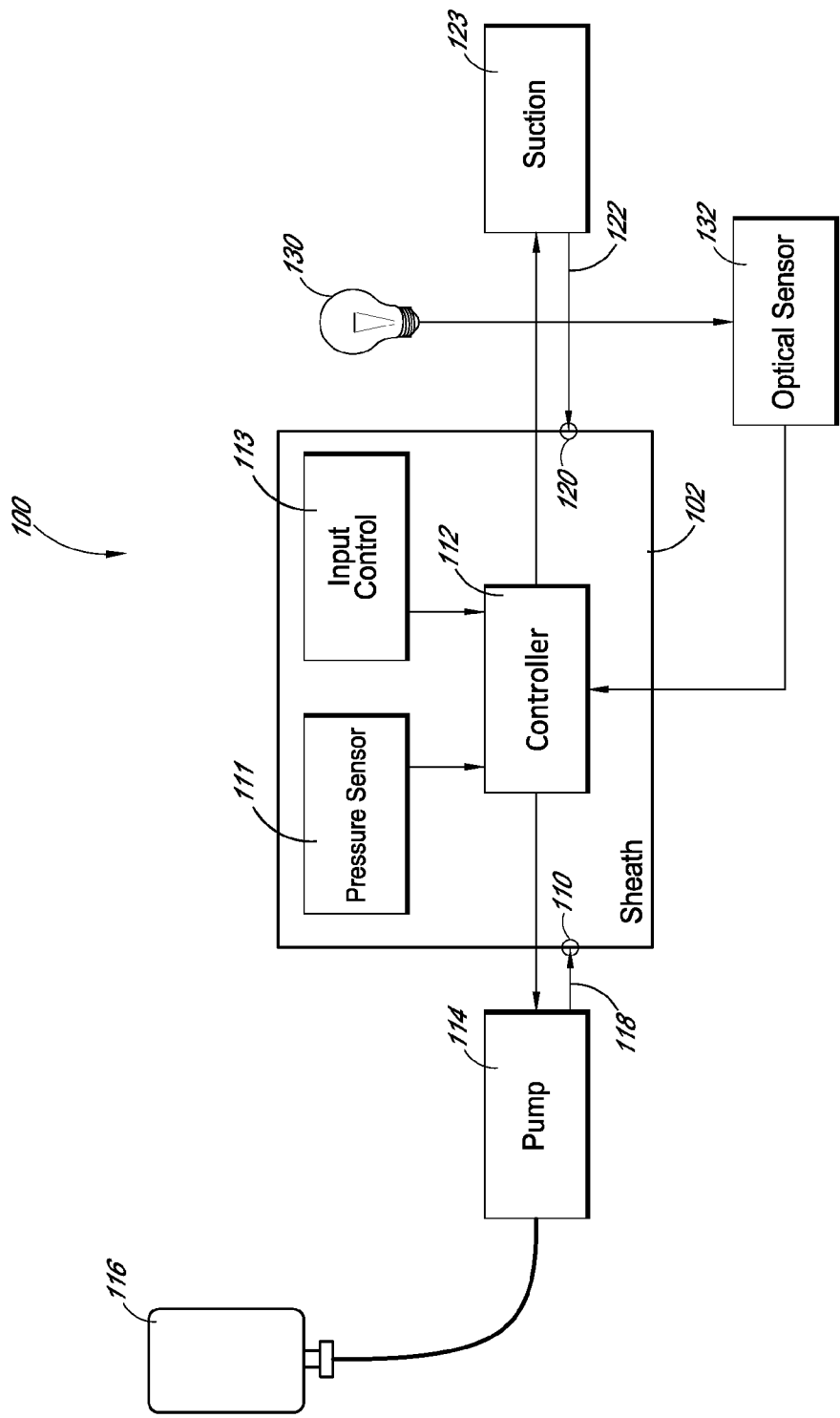
FIG. 14 is a schematic representation of a pressure-controlling sheath.

FIG. 14 illustrates a schematic diagram of a pressure-controlling sheath system 100. Although not shown, the sheath 102 can include a cap 4, 4' with any of the features described above.

The sheath 102 can include one or more ports 110, 120 positioned near or at a proximal or external end of the sheath 102 or in the cap 4, 4'. The sheath 102 can include an inflow port 110 that provides access to an inflow channel extending along at least a portion of a length of the sheath 102, and/or an outflow port 120 that provides access to an outflow channel extending along at least a portion of the length of the sheath 102. The inflow and outflow channels could extend along an exterior of the sheath 102, within the walls of the sheath 102, through separate lumens in the sheath 102, or be the main lumen of the sheath 102. If the inflow and/or outflow channels are separate from the main lumen of the sheath 102, the inflow and/or outflow channels can flow into the main lumen along any portion of the sheath 102 or flow out of a distal end of the sheath 102.

If the sheath 102 includes both an inflow port 110 and an outflow port 120, the inflow and outflow ports 110, 120 can be about the same size or different sizes. For example, the inflow port 110 can be larger than the outflow port 120, such that the inflow rate is much greater than the outflow rate. In this configuration, even if the suction is working through the outflow port 120 and the ultrasonic lithotripsy port simultaneously, the inflow would still be able to maintain a set renal pressure in the collecting system.

The inflow and outflow ports 110, 120 can be rigid and/or attached at right angles to the sheath. For example, the inflow and outflow ports 110, 120 can be flanges positioned on or connected to the sheath 102 such that flexible inflow tubing 118 or outflow tubing 122 can be attached to a respective port 110, 120. When the inflow tubing 118 and/or outflow tubing 122 is connected to the respective port 110, 120, it may be desirable to include one or more tripods (not shown) to support the tubing 118, 122, so that the sheath 102 is not inadvertently removed. Each tripod can be adjusted to the level of the sheath 102. Further, each tripod can include a groove to support the tubing 118, 120.

The inflow port 110 can be sized to allow sufficient irrigation fluid to flow from a saline bottle 116 and through the port 110 with the aid of a pump 114. The saline bottle 116 can hold at least about 4 liters, for example, about 4 liters, about 5 liters, or about 6 liters. The inflow tubing 118 can extend from the saline bottle 116 to the port 110. The inflow tubing 118 can connect to the saline bottle 116 and/or port 110 using a screw fit, friction fit, luer, or other conventional mechanism. The connections can be reinforced with a ferrule, clip, or other reinforcing feature. The inflow tubing 118 can be a high flow warming tubing that allows for high irrigation flow of warm fluid to prevent the patient's body temperature from dropping despite this rapid flow of fluid. Further, the inflow tubing 118 can have a diameter sized to decrease resistance to fluid flow, for example, between about 6 mm and 12 mm, such as between about 8 mm and about 10 mm.

The outflow port 120 can be sized to allow fluid to flow out of the port to maintain visualization within the collecting system in the body. The outflow tubing 122 can be connected to the outflow port 120 using a screw fit, friction fit, luer, or other conventional mechanism. The connection can be reinforced with a ferrule, clip, or other reinforcing feature. Without a suction source, fluid can flow out of the outflow port 120 passively by gravity and pressure gradients. The outflow tubing 122 can be connected to a container to prevent the spillage of fluid in the operating room. This fluid could also be recycled after being filtered and cycled back into the inflow channel.

As shown in FIG. 14, the outflow tubing 122 can be connected to a source of suction 123. For example, the outflow tubing 122 can be connected to a suction canister 123 having a high-flow semi-permeable membrane that can filter blood products, bacteria, and/or stone pieces and allow the irrigation fluid to be re-infused, thereby maintaining a closed system and allowing recycling of irrigation fluid. This can be more cost effective and reduce down time associated with replacing the saline bottles. This mechanism could include a trap to allow stone crystals to be collected to be sent for chemical analysis. In addition, the stone pieces could be cultured to allow the bacterial organisms inside the stones to be determined so that the patients could be placed upon the appropriate antibiotics. Alternatively or in addition to the source of suction, the outflow tubing 122 can include a valve that can control outflow through the tubing 122.

The sheath 102 can include one or more pressure sensors 111 configured to detect the pressure in the system (see FIG. 14). Although FIG. 14 illustrates the pressure sensor 111 as being within the sheath 102, the pressure sensor 102 can be disposed anywhere along the system 100, including along the inflow tubing 118 or the outflow tubing 122 or in both places. The pressure sensor 111 can be disposed at or near a distal end of the sheath 102, along an intermediate portion of the sheath 102, at or near a port 110, 120, at or near a proximal end of the tubing 118, 122, or otherwise. For example, the pressure sensor 111 could be placed upon the tip of the nephroscope in a position where the fluid infusing and the suction would not have a direct effect on the pressure measurement. The pressure measurements can be transmitted to a controller 112 in the sheath 102 or coupled to the sheath 102. The pressure sensor 111 can be hardwired to transmit information along the system 100 to the controller 112 or to transmit the information wirelessly.

The controller 112 can include a processor configured to calculate the pressure within the collecting system in the body based on the pressure sensor measurement and subsequently automatically control fluid inflow and outflow based on the pressure measurement. This can be helpful where high flow is needed to clear bleeding, but pressure must still be maintained to have a tamponade effect upon venous bleeding. This could also be configured and operated in the fluid conservation mode if the fluid were not being recycled so that the pressure could be maintained with minimal flow of irrigation fluid.

The sheath 102 can include an input control 113 disposed near a proximal end of the sheath 102. The surgeon can enter a desired renal collecting system pressure into the input control 113. In order to minimize bleeding while still providing collecting system distention but avoiding rupture or pyelovenous backflow, the desired pressure can be between about 25 mm Hg and 40 mm Hg in patients with metabolic (noninfectious stones), and somewhat lower, such as between about 15 mm Hg and about 30 mm Hg in patients with infected stones. Based on the pressure sensor measurements, the controller 112 can control, by various algorithms, the inflow and outflow of fluid through the sheath 102, thereby controlling the pressure in the collecting system. If the collecting system pressure exceeds the desired pressure, fluid flow out of the outflow port 120 can be turned on or increased until the pressure decreases to the desired level. Once the desired pressure is achieved, the outflow of saline can be automatically decreased or stopped. If the pressure is too low, the pump 114 can begin pumping or increase pumping from a saline bottle 116 via the port 110 until the desired pressure is achieved. Once the desired pressure is achieved, the inflow of saline can be automatically decreased or stopped.

The controller 112 can take into consideration the amount of visibility in the renal collecting system. For example, one or more optical sensors 132 on the sheath 102 or connected to the sheath 102 can sense when the visibility is not clear and automatically adjust the inflow and/or outflow to maintain a clear irrigation field and a set pre-established pressure. A light 130 could be shined across the outflow tubing 122, inflow tubing 118, and/or sheath 102 and registered by an optical sensor 132 positioned opposite the light emitter (see FIG. 14). Blood or debris that decreases the absorption of light by the sensor could signal the controller 112 to increase the rate of suction by the source of suction 123 and to increase the pump rate of the pump 114 to increase inflow, thereby maintaining the same pressure and improving visibility.

The sheath 102 can employ a similar process as illustrated in FIGS. 12 and/or 13. Although the flow charts in FIGS. 12 and 13 illustrate a feedback mechanism for controlling both inflow and outflow, in some instances, the sheath 102 only includes an inflow port 110 or an outflow port 120. In some instances, even if the sheath 102 includes both inflow and outflow ports 110, 112, the controller 112 only controls fluid through one port. For example, the controller 112 may control fluid inflow through the inflow port 110 based on the pressure readings, but fluid outflow through the outflow port may be continuous at all times, passively by gravity and pressure gradients. Alternatively, the outflow can be controlled by the operator (e.g., slow, medium or high flow), while the inflow can automatically adjust the inflow to a rate to maintain the pressure that was set, or vice versa. Outflow or inflow can be set to a scale such as 1-10, or a rate of flow such as 1 cc/sec/5 cc/sec/10 cc/sec, etc.

Pressure Controlling Endoscope

Figure 15:
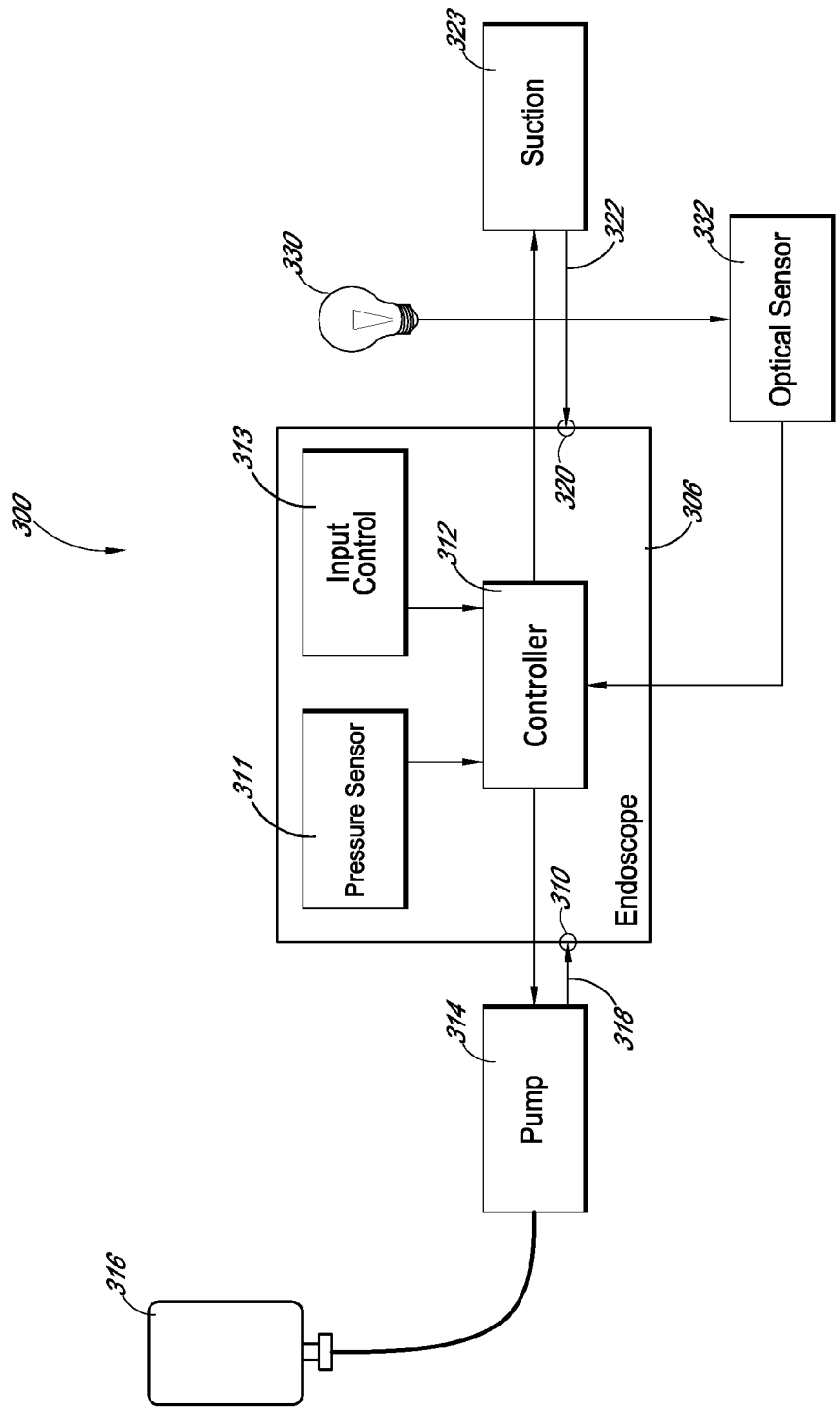
FIG. 15 is a schematic representation of a pressure-controlling endoscope.

FIG. 15 illustrates a schematic diagram of a pressure-controlling endoscope system 300. Although not shown, the sheath can include a cap 4, 4' with any of the features described above, through which the endoscope 306 can extend (see FIG. 3).

Depending on the size of the patient, the endoscope 306 can be at least about 15 cm long and/or less than or equal to about 30 cm long, for example, between about 15 cm and about 20 cm, between about 20 cm and about 25 cm, or between about 25 cm and about 30 cm.

The endoscope 306 can include a diameter that is between about 15 F and about 30 F, for example, between about 16 F and 18 F, between about 18 F and 20 F, between about 20 F and about 22 F, between about 22 F and about 24 F, between about 24 F and about 26 F, between about 26 F and about 28 F, or between about 28 F and about 30 F. As an example, the endoscope 306 can be about 20 cm long and have an outer diameter of about 24 F or 26 F.

The endoscope 306 can include one or more working lumens. Depending on the size of the endoscope 306, the endoscope 306 can include a working lumen that is at least about 9 F and/or less than or equal to about 22 F.

The endoscope 306 can be constructed from stainless steel or any other suitable medical grade material.

The endoscope 306 can include a conventional rod lens. Alternatively, a fiber optic bundle can convey the image to the surgeon. The image can be captured by a CMOS or "chip on a stick" technology and delivered electronically. The endoscope can also include any of the camera features described in U.S. Publication No. 2014/0309677, filed Apr. 10, 2014, which is hereby incorporated by reference in its entirety.

The endoscope 306 can include one or more ports 310, 320 near or at a proximal end of the endoscope 306. For example, the endoscope 306 can include an inflow port 310 and/or an outflow port 320. The inflow and outflow ports 310, 320 can be about the same size or different sizes. In some instances, the inflow port 310 can be larger than the outflow port 320.

The inflow port 310 can be sized to allow sufficient irrigation fluid to flow from a saline bottle 316 and through the port 310 with the aid of a pump 314. The saline bottle 316 can hold at least about 4 liters, for example, about 4 liters, about 5 liters, or about 6 liters. Inflow tubing 318 can extend from the saline bottle 316 to the port 310. The inflow tubing 318 can connect to the saline bottle 316 and/or port 310 using a screw fit, friction fit, luer, or other conventional mechanism. The connections can be reinforced with a ferrule, clip, or other reinforcing feature.

The inflow tubing 318 can have a diameter sized to decrease resistance to fluid flow, for example, between about 6 mm and 12 mm, such as between about 8 mm and 10 mm. In some configurations, it may be desirable to use a high flow warming tubing that facilitates high irrigation flow.

Although not shown, the inflow port 310 can provide access to an inflow channel extending from the port 310 to a distal portion of the endoscope 306. In some configurations, the inflow channel can be shaped as a ring surrounding an outer periphery of the endoscope 306. A distal end of the inflow channel can be configured (e.g., tapered) to direct the irrigant inward to stabilize the kidney stone at the center of the working area.

In some configurations, the inflow channel can extend from the port to the distal portion of the endoscope 306. At the distal portion of the endoscope 306, the inflow channel can include a number of exit openings positioned to form a ring. The ring can surround an outer periphery of an end face of the endoscope 306. Each opening can be angled such that the irrigation fluid converges at a focal point, for example, about 1 to 2 cm from the end of the endoscope.

In some configurations, the irrigation inflow channel can be positioned off center from the central axis of the endoscope 306. The inflow channel can be positioned at a 6 o'clock position relative to the image sensor to avoid obstructing the image. The inflow channel should be sized to allow rapid infusion of fluid. Depending on the size of the endoscope, the inflow channel can have a lumen sized between about 6 F and 20 F, for example, between about 6 F and about 8 F, between about 8 F and about 10 F, between about 10 F and about 12 F, between about 12 F and about 14 F, between about 14 F and about 16 F, between about 16 F and about 18 F, or between about 18 F and about 20 F.

In some configurations, the inflow channel can be distinct from the endoscope 306 and can extend toward an end portion of the endoscope to prevent inadvertent cycling of the fluid from the infusion port to the outflow port without entering the collecting system of the kidney. The inflow channel can include a diameter large enough to maintain the pressure even when the ultrasonic or other probe is suctioning.

Although not shown, the outflow port 320 can provide access to an outflow channel extending from the port to a distal portion of the endoscope 306. The outflow port 320 can be sized to allow fluid to flow out of the port 320 to maintain visualization within the collecting system. Outflow tubing 322 can be connected to the outflow port 320 using a screw fit, friction fit, luer, or other conventional mechanism. The connection can be reinforced with a ferrule, clip, or other reinforcing feature. Without a suction source, fluid can flow out of the outflow port 320 passively by gravity and pressure gradients. The outflow tubing 322 can be connected to a container to prevent the spillage of fluid in the operating room.

As shown in FIG. 15, the outflow tubing 322 can be connected to a source of suction 323. For example, the outflow tubing 322 can be connected to a suction canister. If the surgeon is working without the ultrasonic lithotripter or other methods of suctioning out stone fragments, the separate source of suction 323 can be used to suction at a rate to keep the field clear.

The outflow channel can have a lumen sized between about 4 F and about 16 F, for example, between about 10 F and about 13 F. In some instances, the outflow channel can be smaller than the inflow channel.

Outflow through the outflow channel can be turned on and off. If there is suitable visualization, outflow can be turned off by closing a valve or turning off suction. When bleeding increases, the surgeon can turn on the outflow by opening the valve or turning on suction. In some instances, the surgeon can manually control the flow rate by increasing or decreasing the size of a valve opening or controlling the level of suction. In some configurations, instead of or in addition to an outflow channel, an ultrasonic lithotripter can be introduced through the working lumen and used to remove fluid.

Instead of a separate outflow channel, the suction source 323 can be attached to the general working port lumen and just suction out through the working lumen. In this configuration, the endoscope 306 may only include a single inflow port 310 or include two ports 310, 320 for inflow. For example, if the ultrasonic lithotripter is being used through the scope, the ultrasonic lithotripter can be used for suction and both ports 310, 320 can simultaneously be used for inflow to maintain the pressure at the prescribed setting. Two different saline sources can be attached to the ports 310, 320.

As shown in FIG. 15, the endoscope 306 can include one or more pressure sensors 314 configured to detect the pressure within the renal collecting system. The pressure sensor 314 can be disposed anywhere along the system 300. For example, the pressure sensor 314 can be disposed at or near a distal end of the endoscope 306, along an intermediate portion of the endoscope 306, at or near a port 310, 320, near a proximal end of the tubing 318, 322, or otherwise. The pressure measurements can be transmitted to a controller 312 disposed at a proximal portion of the endoscope 306. The pressure sensor 314 can be hardwired to transmit information to the controller 312 or wirelessly transmit information to the controller 312.

The controller 312 can include a processor configured to calculate the pressure within the renal collecting system based on the pressure sensor measurement and control fluid inflow and/or outflow based on the collecting system pressure. This can be helpful where high flow is needed to clear bleeding, but pressure must still be maintained to have a tamponade effect upon venous bleeding.

The controller 312 can take into consideration the amount of visibility in the renal collecting system. For example, one or more optical sensors 332 on the endoscope 306 or connected to the sheath can sense when the visibility is not clear and automatically adjust the inflow and/or outflow to maintain a clear irrigation field and a set pre-established pressure. A light 330 could be shined across the outflow tubing 322, inflow tubing 318, and/or endoscope 306 and registered by an optical sensor 332 positioned opposite the light emitter (see FIG. 15). Blood or debris that decreases the absorption of light by the sensor could signal the controller 312 to increase the rate of suction by the source of suction 323 and to increase the pump rate of the pump 314 to increase inflow, thereby maintaining the same pressure and improving visibility.

The endoscope 306 can include an input control 313 disposed near a proximal end of the endoscope 306. The surgeon can enter a desired collecting system pressure into the input control. In order to minimize bleeding while still providing collecting system distention and avoiding rupture or pyelovenous backflow, the optimal pressure can be between about 25 mm Hg and about 40 mm Hg in patients with metabolic (noninfectious stones) and somewhat lower, such as between about 15 mm Hg and about 30 mm Hg in patients with infected stones. Based on the pressure sensor measurements, the controller 312 can control, by various algorithms, the inflow and outflow of fluid through the endoscope, thereby controlling the pressure in the renal collecting system. If the collecting system pressure exceeds the desired pressure, fluid flow out of the outflow port 320 can be turned on or increased until the pressure decreases to the desired level. Once the desired pressure is achieved, the outflow of saline can be automatically decreased or stopped. If the pressure is too low, the pump 314 can begin pumping or increase pumping from a saline bottle 316 via the port 310 until the desired pressure is achieved. Once the desired pressure is achieved, the inflow of saline can be automatically decreased or stopped.

The endoscope can employ a similar process as illustrated in FIGS. 12 and/or 13. In some instances, the endoscope 306 only includes an inflow port 310 or an outflow port 320. In some instances, even if the endoscope 306 includes both inflow and outflow ports 310, 320, the controller 312 only controls fluid through one port. For example, the controller 312 may control fluid inflow through the inflow port 310 based on the pressure readings, but fluid outflow through the outflow port may be continuous at all times, passively by gravity and pressure gradients. Alternatively, the outflow can be controlled (e.g., slow, medium or high flow), while the inflow can automatically adjust the inflow to a rate to maintain the pressure that was set, or vice versa. Outflow or inflow can be set to a scale such as 1-10, or a rate of outflow such as 1 cc/sec/5 cc/sec/10 cc/sec, etc.

Pressure-Controlling System

Any combination of the cap system, pressure-controlled sheath, and/or pressure-controlled endoscope described above can be used together. If the system includes one or more the pressure-controlled cap, pressure-controlled sheath, and pressure-controlled endoscope, the system can include one or more pressure sensors or optical sensors positioned on the cap, endoscope, and/or the sheath. The cap, sheath, and/or endoscope can control pressure using pressure measurements from different pressure sensors or the same sensor or control visibility based on the amount of detected light from the one or more optical sensors. Further, the system can include one or more inflow and/or outflow ports disposed on the cap, the endoscope, and/or the sheath. For example, the cap, the endoscope, and the sheath can each include inflow and outflow ports. As another example, each of the cap, the endoscope, and/or sheath can include an inflow port or an outflow port. Using these apparatuses together will maintain the optimal flow and clarity of the fluid during the procedure.

Terminology

Although certain embodiments have been described herein with respect to renal procedures, the sheaths and endoscopes described herein can be used during other percutaneous or endoscopic surgeries, such as arthroscopy, percutaneous spine surgery, cystoscopy, ureteroscopy, and hysteroscopy.

As used herein, the relative terms "proximal" and "distal" shall be defined from the perspective of the sheath or endoscope. Thus, proximal refers to the direction of the portion of the sheath or endoscope external to the patient and distal refers to the direction of the portion of the sheath or endoscope within the patient.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately," "about," and "substantially" as used herein represent an amount close to the stated amount that still performs a desired function or achieves a desired result. For example, the terms "approximately," "about," and "substantially" may refer to an amount that is within less than 10% of the stated amount, as the context may dictate.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 30 F" includes "30 F."

Although certain embodiments and examples have been described herein, it will be understood by those skilled in the art that many aspects of the pressure-controlling features shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "positioning a distal end of an endoscope in the collecting system" include "instructing the positioning a distal end of an endoscope in the collecting system."

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently.

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

EXAMPLE EMBODIMENTS

The following example embodiments identify some possible permutations of combinations of features disclosed herein, although other permutations of combinations of features are also possible.

1. A sheath cap assembly configured to enclosed a proximal end of a sheath, the cap comprising:
   a main body portion comprising:
      a wall portion shaped to surround the proximal end of the sheath;
      a closed proximal end portion; and
      an open distal end portion;
   an inflow port on the main body portion, the inflow port providing access from an irrigation source to a lumen of the sheath when the sheath cap is secured to the sheath;
   an outflow port on the main body portion, the outflow port providing an outlet for fluid flowing out of the sheath when the sheath cap is secured to the sheath;
   a pressure sensor connected to the sheath cap, the pressure sensor configured to generate a pressure measurement; and
   a processing unit configured to direct fluid through at least one of the inflow port and the outflow port based on the pressure measurement.

2. The sheath cap assembly of Embodiment 1, wherein the closed proximal end portion comprises an opening through which an endoscope can be introduced.

3. The sheath cap assembly of Embodiment 2, wherein the opening comprises a sealing structure configured to form a seal around the endoscope when the endoscope is introduced through the opening.

4. The sheath cap assembly of any one of Embodiments 1 to 3, further comprising a closure mechanism configured to secure the sheath cap to the sheath.

5. The sheath cap assembly of any one of Embodiments 1 to 4, wherein the pressure sensor is positioned in the outflow port.

6. The sheath cap assembly of any one of Embodiments 1 to 5, further comprising outflow tubing connected to the outflow port.

7. The sheath cap assembly of Embodiment 6, wherein the pressure sensor is positioned in the outflow tubing.

8. The sheath cap assembly of any one of Embodiments 1 to 7, further comprising a light transmitter configured to transmit light across fluid flowing out of the sheath.

9. The sheath cap assembly of Embodiment 8, further comprising an optical sensor configured to detect an amount of light absorbed by the fluid flowing out of the sheath.

10. The sheath cap assembly of Embodiment 8, wherein the processing unit is configured to direct fluid flow through the inflow port or the outflow port based on the detect amount of light absorbed.

11. The sheath cap assembly of Embodiment 8, further comprising outflow tubing connected to the outflow port, the light transmitter positioned to transmit light across the outflow tubing.

12. The sheath cap assembly of any one of Embodiments 1 to 11, wherein the processing unit is configured to determine a pressure at a distal end of the sheath based on the pressure measurement.

13. A sheath cap assembly configured to enclosed a proximal end of a sheath, the cap comprising:
    a main body portion comprising:
       a wall portion shaped to surround the proximal end of the sheath;
       a closed proximal end portion; and
       an open distal end portion;
    an inflow port on the main body portion, the inflow port providing access from an irrigation source to a lumen of the sheath when the sheath cap is secured to the sheath;

an outflow port on the main body portion, the outflow port providing an outlet for fluid flowing out of the sheath when the sheath cap is secured to the sheath;

a light transmitter configured to transmit light across the fluid flowing out of the sheath;

an optical sensor configured to detect an amount of light absorbed by the fluid flowing out of the sheath; and a processing unit configured to direct fluid through at least one of the inflow port and the outflow port based on the detected amount of absorbed light.

14. The sheath cap assembly of Embodiment 13, wherein the closed proximal end portion comprises an opening through which an endoscope can be introduced.

15. The sheath cap assembly of Embodiment 14, wherein the opening comprises a sealing structure configured to form a seal around the endoscope when the endoscope is introduced through the opening.

16. The sheath cap assembly of any one of Embodiments 13 to 15, further comprising a closure mechanism configured to secure the sheath cap to the sheath.

17. The sheath cap assembly of any one of Embodiments 13 to 16, wherein the optical sensor is positioned in the outflow port.

18. The sheath cap assembly of any one of Embodiments 13 to 17, further comprising outflow tubing connected to the outflow port.

19. The sheath cap assembly of Embodiment 18, wherein the optical sensor is connected to the outflow tubing.

20. A system for controlling pressure during percutaneous and endoscopic surgery, the system comprising:

an endoscope having a proximal portion and a distal portion, the endoscope comprising:

an inflow port providing access to an inflow channel extending from the inflow port to the distal portion of the endoscope; and an outflow port providing access to an outflow channel extending from the outflow port to the distal portion of the endoscope;

a pressure sensor connected to the endoscope, the pressure sensor configured to generate a pressure measurement; and a processing unit configured to direct fluid through at least one of the inflow port and the outflow port based on the pressure measurement.

21. The system of Embodiment 20, wherein the pressure sensor is in the outflow port of the endoscope.

22. The system of Embodiment 20, wherein the pressure sensor is positioned in a distal section of the endoscope.

23. The system of Embodiment 20 or 21, wherein the endoscope comprises an input control configured to receive a desired pressure value.

24. The system of Embodiment 23, wherein the processing unit is configured to increase flow of an irrigant through the inflow port when the pressure measurement is less than the desired pressure value.

25. The system of Embodiment 23 or 24, wherein the processing unit is configured to increase flow of a fluid out of the outflow port when the pressure measurement is greater than the desired pressure value.

26. The system of any one of Embodiments 20 to 25, wherein the endoscope further comprises a light emitter that transmits light across an outflow of fluid and the optical sensor detects an amount of light absorbed by the outflow of fluid.

27. The system of Embodiment 26, wherein the processing unit is configured to direct fluid inflow or outflow based on the amount of detected light.

28. A system for controlling pressure during percutaneous and endoscopic surgery, the system comprising:

a sheath having a proximal portion and a distal portion, the sheath comprising:

an inflow port providing access to an inflow channel extending from the inflow port to the distal portion of the sheath; and an outflow port providing access to an outflow channel extending from the outflow port to the distal portion of the sheath;

a pressure sensor connected to the sheath, the pressure sensor configured to generate a pressure measurement; and a processing unit configured to control fluid through at least one of the inflow port and the outflow port based on the pressure measurement.

29. The system of Embodiment 28, wherein the pressure sensor is positioned in the outflow port of the sheath.

30. The system of Embodiment 28, wherein the pressure sensor is positioned at a distal section of the sheath.

31. The system of any one of Embodiments 28 to 30, wherein the sheath comprises an input control configured to receive a desired pressure value.

32. The system of Embodiment 31 wherein the processing unit is configured to increase flow of an irrigant through the inflow port when the pressure measurement is less than the desired pressure value.

33. The system of Embodiment 31 or 32, wherein the processing unit is configured to increase flow of a fluid out of the outflow port when the pressure measurement is greater than the desired pressure value.

34. The system of any one of Embodiments 28 to 33, further comprising a cap configured to close a proximal end of the sheath.

35. The system of Embodiment 34, wherein the cap is configured to receive an endoscope.

36. The system of any one of Embodiments 28 to 35, wherein the sheath further comprises a light emitter that transmits light across an outflow of fluid from the sheath and an optical sensor detects an amount of light absorbed by the outflow of fluid.

37. The system of Embodiment 36, wherein the processing unit is configured to adjust fluid inflow or outflow if the detected absorbed light is greater than a prescribed level of light.

38. The system of any one of Embodiments 28 to 37, further comprising an endoscope configured to be introduced through the sheath, the endoscope having a proximal portion and a distal portion, the endoscope comprising:

an endoscopic inflow port providing access to an inflow channel extending from the inflow port to the distal portion of the endoscope;

an endoscopic outflow port providing access to an outflow channel extending from the outflow port to the distal portion of the endoscope;

an endoscopic pressure sensor positioned on the endoscope, the endoscopic pressure sensor configured to generate a second pressure measurement; and an endoscopic processing unit configured to control fluid through at least one of the endoscopic inflow port and the endoscopic outflow port based on the second pressure measurement.

39. A method of controlling pressure in a renal collecting system, the method comprising:

positioning a distal end of an endoscope in the collecting system, the endoscope comprising:

an inflow port providing access to an inflow channel extending from the inflow port to a distal portion of the endoscope;

an outflow port providing access to an outflow channel extending from the outflow port to the distal portion of the endoscope;

a pressure sensor positioned on the endoscope, the pressure sensor configured to generate a pressure measurement; and a processing unit configured to control fluid through at least one of the inflow port and the outflow port based on the pressure measurement; measuring the pressure in the collecting system; and directing fluid flow through at least one of the inflow port and the outflow port based on the pressure measurement.

40. The method of Embodiment 39, further comprising inputting a desired pressure value into an input control of the endoscope.

41. The method of Embodiment 40, further comprising increasing flow of an irrigant through the inflow port when the pressure measurement is less than the desired pressure value.

42. The method of Embodiment 39 or 40, further comprising increasing flow of a fluid out of the outflow port when the pressure measurement is greater than the desired pressure value.

43. The method of any one of Embodiments 39 to 42, further comprising transmitting light through an outflow of fluid and detecting an amount of light absorbed by the outflow of fluid.

44. The method of Embodiment 43, further comprising directing fluid inflow through at least one of the inflow port and the outflow port if the amount of absorbed light is greater than a prescribed level of light.

45. A method of controlling pressure in a renal collecting system, the method comprising:

positioning a distal end of a sheath in the collecting system, the endoscope comprising:

an inflow port providing access to an inflow channel extending from the inflow port to a distal portion of the sheath;

an outflow port providing access to an outflow channel extending from the outflow port to the distal portion of the sheath;

a pressure sensor positioned on the sheath, the pressure sensor configured to generate a pressure measurement; and a processing unit configured to control fluid through at least one of the inflow port and the outflow port based on the pressure measurement;

measuring the pressure in the collecting system; and directing fluid flow through at least one of the inflow port and the outflow port based on the pressure measurement.

46. The method of Embodiment 45, further comprising inputting a desired pressure value into an input control of the endoscope.

47. The method of Embodiment 46, further comprising increasing flow of an irrigant through the inflow port when the pressure measurement is less than the desired pressure value.

48. The method of Embodiment 45 or 46, further comprising increasing flow of a fluid out of the outflow port when the pressure measurement is greater than the desired pressure value.

49. The method of any one of Embodiments 45 to 48, further comprising transmitting light across an outflow of fluid and detecting an amount of light absorbed by the outflow of fluid.

50. The method of Embodiment 49, further comprising directing fluid inflow through at least one of the inflow port and the outflow port if the amount of absorbed light is greater than a prescribed level of light.

What is claimed is:

1. A system for controlling pressure during percutaneous kidney surgeries by converting an open percutaneous surgical procedure into a closed surgical procedure, the system comprising:

a sheath comprising a proximal end and a distal end, the distal end of the sheath having an elongate percutaneous insertion section for insertion through the skin of the patient and extending to a surgical site, the sheath having a cross-sectional dimension configured to receive endoscopes of various diameters therethrough, the sheath and endoscope forming a space defining an open passage for irrigation outflow;

a removable cap configured to engage the proximal end of the sheath, the cap comprising:

a main body portion comprising:

a circumferential pliable wall portion shaped to surround the proximal end of the sheath, the wall portion configured to engage sheaths of various dimensions, at least one sheath dimension comprising 30 French;

a proximal end portion comprising an opening through which an endoscope can be introduced, the opening configured to form a seal around the endoscope, the opening being configured to receive endoscopes of various dimensions;

an open distal end portion, and a closure mechanism mounted on the wall portion of the cap and configured to apply circumferential pressure to the cap to secure it to the proximal end of the sheath, the closure mechanism having an open position which does not apply cinching pressure to the cap, and a closed position which does apply cinching pressure to the cap, the closure system when in the open position providing replaceability of the cap on the sheath or other sheaths;

the main body portion of the cap and the proximal end portion defining a closure of the passage at the proximal end of the sheath;

an inflow port extending from the main body portion, the inflow port providing access from an irrigation source, the irrigation source including a pump to supply irrigation fluids to the lumen of the sheath;

an outflow port extending from the main body portion, the outflow port providing an outlet for fluid flowing out of the sheath when the sheath cap is secured to the sheath, the outflow port being in fluid communication with a suction device;

a pressure sensor connected to the sheath cap, the pressure sensor configured to generate a pressure measurement of the internal renal pelvic pressure at the surgical site within the patient;

a user input control associated with the sheath to allow a user to input a desired internal pressure target; and a processing unit in communication with the pressure sensor, the user input control, the pump, and the suction device, the processing unit configured to direct fluid through at least one of the inflow port and the outflow port based on the pressure measurement to maintain the desired input pressure target, wherein the processing unit is configured to maintain a renal pelvic pressure at least in the range of about 15 mmHg and about 40 mmHg.

2. The sheath cap assembly of claim 1, wherein the opening comprises a self-sealing structure configured to form a seal around the endoscope when the endoscope is introduced through the opening, the seal comprising a slit valve or flap valve.

3. The sheath cap assembly of claim 1, wherein the pressure sensor is positioned in the outflow port.

4. The sheath cap assembly of claim 1, further comprising outflow tubing connected to the outflow port.

5. The sheath cap assembly of claim 4, wherein the pressure sensor is positioned in the outflow tubing.

6. The sheath cap assembly of claim 1, further comprising a light transmitter configured to transmit light across fluid flowing out of the sheath.

7. The sheath cap assembly of claim 6, further comprising an optical sensor configured to detect an amount of light absorbed by the fluid flowing out of the sheath.

8. The sheath cap assembly of claim 6, wherein the processing unit is configured to direct fluid flow through the inflow port or the outflow port based on the detect amount of light absorbed.

9. The sheath cap assembly of claim 6, further comprising outflow tubing connected to the outflow port, the light transmitter positioned to transmit light across the outflow tubing.

10. A system for controlling pressure during percutaneous kidney surgeries by converting an open percutaneous surgical procedure into a closed surgical procedure, the system comprising:
- a sheath comprising a proximal end and a distal end, the distal end of the sheath having an elongate percutaneous insertion section for insertion through the skin of the patient and extending to a surgical site, the sheath having a cross-sectional dimension configured to receive endoscopes of various diameters therethrough, the sheath and endoscope forming a space defining an open passage for irrigation outflow;
- a removable cap configured to engage the proximal end of the sheath, the cap comprising:
- a main body portion comprising:
    - a circumferential pliable wall portion shaped to surround the proximal end of the sheath, the wall portion configured to engage sheaths of various dimensions, at least one sheath dimension comprising 30 French;
    - a proximal end portion comprising an opening through which an endoscope can be introduced, the opening configured to form a seal around the endoscope, the opening being configured to receive endoscopes of various dimensions;
    - an open distal end portion; and
    - a closure mechanism mounted on the wall portion of the cap and configured to apply circumferential pressure to the cap to secure it to the proximal end of the sheath, the closure mechanism having an open position and a closed position, the closure system when in the open position providing replaceability of the cap on the sheath or other sheaths;
    - the main body portion of the cap and the proximal end portion defining a closure of the passage at the proximal end of the sheath
- an inflow port extending from the main body portion, the inflow port providing access from an irrigation source, the irrigation source including a pump to supply irrigation fluids to the lumen of the sheath;
- an outflow port extending from the main body portion, the outflow port providing an outlet for fluid flowing out of the sheath when the sheath cap is secured to the sheath, the outflow port being in fluid communication with a suction device;
- a light transmitter configured to transmit light across the fluid flowing out of the sheath;
- an optical sensor configured to detect an amount of light absorbed by the fluid flowing out of the sheath; and
- a processing unit in communication with the optical sensor, the user input control, the pump, and the suction device, the processing unit configured to direct fluid through at least one of the inflow port and the outflow port based on the detected amount of absorbed light.

11. The sheath cap assembly of claim 10, wherein the opening comprises a self-sealing structure configured to form a seal around the endoscope when the endoscope is introduced through the opening, the seal comprising a slit valve or flap valve.

12. The sheath cap assembly of claim 10, further comprising a closure mechanism configured to secure the sheath cap to the sheath.

13. The sheath cap assembly of claim 10, wherein the optical sensor is positioned in the outflow port.

14. The sheath cap assembly of claim 10, further comprising outflow tubing connected to the outflow port.

15. The sheath cap assembly of claim 14, wherein the optical sensor is connected to the outflow tubing.

* * * * *